(12) United States Patent
Lehmann et al.

(10) Patent No.: US 9,841,013 B2
(45) Date of Patent: Dec. 12, 2017

(54) TEST CONTROLLER FOR A ROTARY PUMP

(75) Inventors: Kirk A. Lehmann, Aachen (DE);
Oliver K. Marseille, Aachen (DE);
Christian W. Vohburger, Geltendorf (DE)

(73) Assignee: CircuLite, Inc., Teaneck, NJ (US)

( * ) Notice: Subject to any disclaimer, the term of this patent is extended or adjusted under 35 U.S.C. 154(b) by 1813 days.

(21) Appl. No.: 13/017,205

(22) Filed: Jan. 31, 2011

(65) Prior Publication Data

US 2011/0200451 A1    Aug. 18, 2011

Related U.S. Application Data

(60) Provisional application No. 61/304,930, filed on Feb. 16, 2010.

(51) Int. Cl.
*H02P 3/00* (2006.01)
*F04B 49/00* (2006.01)
(Continued)

(52) U.S. Cl.
CPC .......... *F04B 51/00* (2013.01); *F04D 15/0088* (2013.01); *A61M 1/101* (2013.01); *F04B 2203/0209* (2013.01)

(58) Field of Classification Search
CPC ... G06F 1/206; H02P 7/29; H02P 6/08; H05K 7/20209
(Continued)

(56) References Cited

U.S. PATENT DOCUMENTS 3,873,252 A * 3/1975 Motomura et al. ........... 418/126
5,352,180 A   10/1994 Candelon et al.
(Continued)

FOREIGN PATENT DOCUMENTS

EP    1067335 A1   1/2001
JP    2008280921 A  11/2008
(Continued)

OTHER PUBLICATIONS

U.S. Patent and Trademark Office, International Preliminary Report on Patentability in PCT Application Serial No. PCT/US11/23132, dated Aug. 7, 2012.
(Continued)

*Primary Examiner* — Eduardo Colon Santana
*Assistant Examiner* — Gabriel Agared
(74) *Attorney, Agent, or Firm* — Wood Herron & Evans LLP

(57) ABSTRACT

A test controller and method to operate a rotary motor of a pump are provided. The test controller includes a test speed circuit electrically coupled to, but detachable from, the pump and being configured to apply at least one signal to the pump motor to cause the pump motor to rotate at a predetermined test speed and/or for a predetermined test time. An actuator selectively activates the test speed circuit to operate the pump motor at the predetermined test speed and/or for the predetermined test time. The method includes electrically coupling the test controller to the pump and, in response to selective activation of the actuator, selectively activating the test speed circuit to apply at least one signal to the pump motor to operate the pump motor at a predetermined test speed and/or for a predetermined test time. The method further includes detaching the test controller from the pump.

30 Claims, 7 Drawing Sheets

(51) Int. Cl.
*F04B 43/12* (2006.01)
*F04B 51/00* (2006.01)
*F04D 15/00* (2006.01)
*A61M 1/10* (2006.01)

(58) Field of Classification Search
USPC ..................................... 318/268; 417/42, 53
See application file for complete search history.

(56) References Cited

U.S. PATENT DOCUMENTS

| | | | |
|---|---|---|---|
| 5,925,992 | A | 7/1999 | Orton |
| 7,083,544 | B2 * | 8/2006 | Goransson et al. ............. 477/3 |
| 2004/0243310 | A1 * | 12/2004 | Griffin et al. .................. 702/10 |
| 2007/0156006 | A1 * | 7/2007 | Smith et al. .................... 600/16 |
| 2009/0132184 | A1 | 5/2009 | Miyakoshi et al. |
| 2011/0178361 | A1 * | 7/2011 | Yomtov .......................... 600/16 |

FOREIGN PATENT DOCUMENTS

| | | |
|---|---|---|
| JP | 2008543378 A | 12/2008 |
| JP | 2011523983 A | 8/2011 |
| WO | 9814225 A2 | 4/1998 |
| WO | 2006133409 A2 | 12/2006 |

OTHER PUBLICATIONS

U.S. Patent and Trademark Office, International Search Report and Written Opinion in PCT Application Serial No. PCT/US11/023132, dated Mar. 25, 2011
Japanese Patent Office, Office Action in JP Application No. 2012-553923, dated Jul. 22, 2014.
Canadian Intellectual Property Office, Office Action in CA 2787941, dated Nov. 23, 2016.
Japanese Patent Office, Office Action in JP Application No. 2012-553923, dated Sep. 26, 2016.

* cited by examiner

TEST CONTROLLER FOR A ROTARY PUMP

CROSS-REFERENCE TO RELATED APPLICATION

This application claims the priority of U.S. Provisional Patent Application Ser. No. 61/304,930, filed on Feb. 16, 2010 (pending), the disclosure of which is incorporated by reference herein.

FIELD OF THE INVENTION

The invention relates generally to testing the operation of a rotary pump. More specifically, the present invention relates to devices and methods for testing the operation of implantable pumps prior to implantation.

BACKGROUND OF THE INVENTION

Rotary pump devices are often used to assist the blood flow of patients. Typically, these devices are implanted in body of a patient and are supplied power by a separate power supply. Generally, one end of the device is attached to the heart of a patient (through a flexible cannula) while another end is attached to a vein or artery of the patient (also through a flexible cannula). When the pump receives power, it assists in the circulation of blood through the patient by transferring blood from one portion of the patient's body to another.

Prior to implantation of the devices, it is often desirable to visually confirm the operation of the device, despite the high levels of quality control that is implemented by device manufacturers to ensure device reliability. As such, users may attempt to connect the devices to their power supply. Thus, the devices are run at their predetermined operating speed "dry" (e.g., without any fluid moving through the device) which can result in accelerated wear of the device due to increased friction. To counteract this problem, some users may insert the device into a sterile fluid bath, but these sterile fluid baths can result in an increased risk of infection to a patient.

Furthermore, the devices often use sensorless speed control methodologies to maintain their speed independent of their load. In particular, reverse electromotive force methodologies (e.g., "back-EMF" methodologies) are often used to maintain the commutation of a brushless motor in the device at a predetermined operating speed. However, to test the devices, the user may not provide enough power for the devices to properly utilize back-EMF methodologies. For example, at a reduced voltage to reduce the speed at which the devices operate, there is often not enough back-EMF generated by the pump motor to maintain speed control, which may result in a pump motor stoppage (resulting in a false device failure diagnosis) or pump motor overspeed (resulting in possible device damage).

There is thus a need for an improved method of testing rotary pump devices for visual verification of their operation.

SUMMARY OF THE INVENTION

Embodiments of the present invention include a test controller for operating a rotary pump motor of a pump, the rotary pump motor having a predetermined operating speed. The test controller includes a test speed circuit electrically coupled to, but detachable from, the pump and being configured to apply at least one signal to the pump motor to cause the pump motor to rotate at a predetermined test speed that is lower than the predetermined operating speed of the pump motor. The test controller further includes an actuator configured to selectively activate the test speed circuit to operate the pump motor to rotate at the predetermined test speed.

Alternative embodiments of the present invention include a test controller for operating a rotary pump motor of a pump having a predetermined operating speed. The test controller includes a test speed circuit electrically coupled to, but detachable from, the pump and being configured to apply at least one signal to the pump motor to cause the pump motor to rotate for a predetermined test time. The test controller further includes an actuator configured to selectively activate the test speed circuit to operate the pump motor for the predetermined test time.

One alternative embodiment of the present invention includes a method for testing the operation of a rotary pump motor of a pump with a test controller, the test controller including a test speed circuit and an actuator. The method includes electrically coupling the test controller to the pump and, in response to selective activation of the actuator, selectively activating the test speed circuit to apply at least one signal to the pump motor to cause the pump motor to rotate at a predetermined test speed that is lower than a predetermined operating speed of the pump motor. The method further includes detaching the test controller from the pump.

Another alternative embodiment of the present invention includes a method for testing the operation of a rotary pump motor of a pump with a test controller, the test controller including a test time circuit and an actuator. The method includes electrically coupling the test controller to the pump and, in response to selective activation of the actuator, selectively activating the test time circuit to apply at least one signal to the pump motor to cause the pump motor to rotate for a predetermined test time that is less than a normal operating time for the pump motor. The method further includes detaching the test controller from the pump.

These and other advantages will be apparent in light of the following figures and detailed description.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention.

It should be understood that the appended drawings are not necessarily to scale, presenting a somewhat simplified representation of various features illustrative of the basic principles of embodiments of the invention. The specific design features of embodiments of the invention as disclosed herein, including, for example, specific dimensions, orientations, locations, connections to circuitry, and shapes of various illustrated components, as well as specific sequences of operations (e.g., including concurrent and/or sequential operations), will be determined in part by the particular intended application and use environment. Certain features of the illustrated embodiments may have been enlarged or distorted relative to others to facilitate visualization and clear understanding.

DETAILED DESCRIPTION

Figure 1:
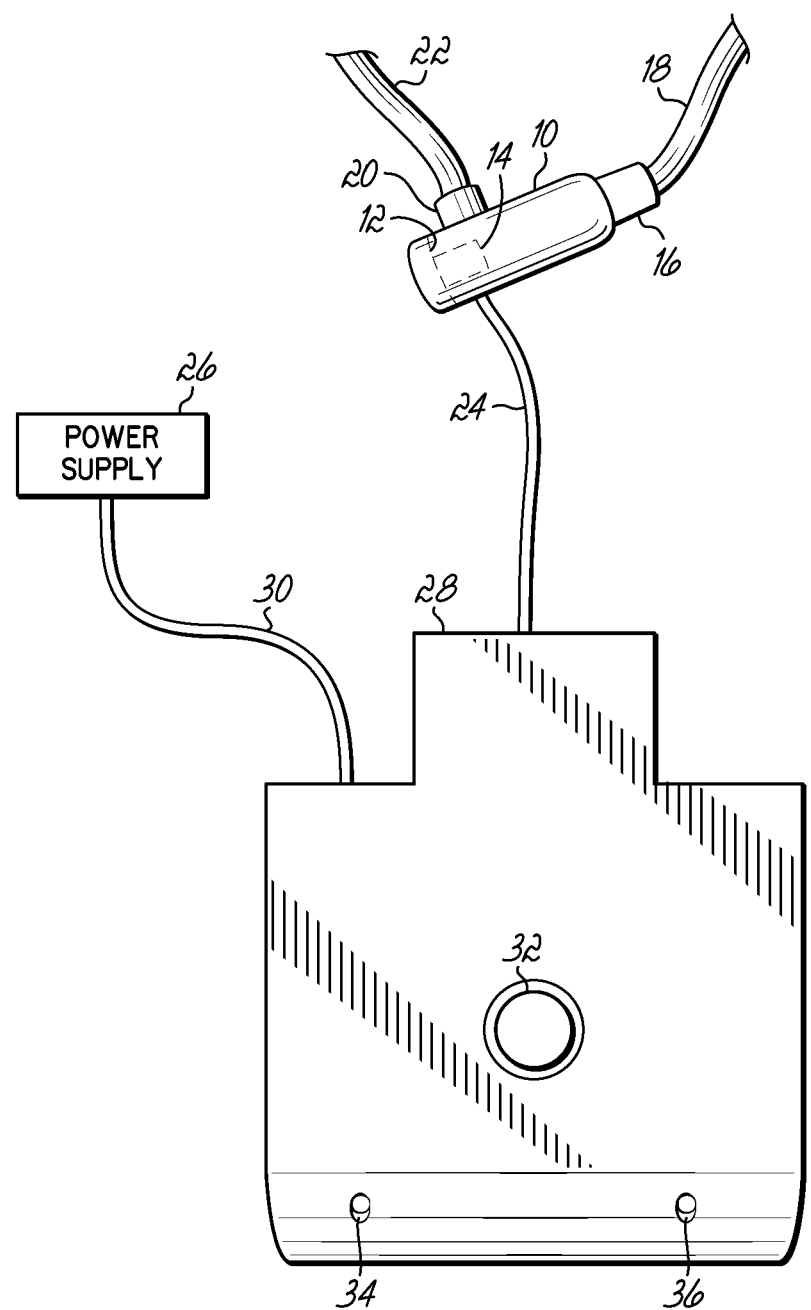
FIG. 1 is an exemplary illustration of a circulatory assist system that includes a rotary pump device, power supply, and test controller consistent with embodiments of the present invention.

Turning to the drawings, wherein like notations denote like parts, FIG. 1 illustrates one embodiment of an implantable rotary pump device 10 (hereinafter, "pump" 10) having a rotary pump motor 12 (hereinafter, "pump motor" 12) and impeller 14. The implantable pump 10 includes an input port 16 to which a flexible input cannula body 18 may be connected to input fluid to the pump 10, as well as an output port 20 to which a flexible output cannula body 22 may be connected to output fluid from the pump 10. A cable 24 extends from the pump 10 to supply power to the pump from either a pump power supply 26 or a pump test controller 28. As illustrated in FIG. 1, the pump 10 receives power through the cable 24 from the pump test controller 28, which in turn receives power from the power supply 26 through a cable 30. When implanted into a patient's body and receiving power directly from the power supply 26, the pump motor 12 is configured to operate from about 20,000 rotations per minute to about 28,000 rotations per minute. As such, and in some embodiments, the pump 10 is a Synergy® Pocket Micro-Pump commercially available from CircuLite, Inc., of Saddle Brook, N.J.

The pump test controller 28 (hereinafter, "controller" 28) is configured to selectively activate the pump 10 and rotate the pump motor 12 at a low speed and/or for limited time intervals such that a user can visually confirm operation of the pump 10 prior to implantation. Thus, the controller 28 includes an actuator 32 to actuate the operation of the pump 10 as well as a controller power indicator 34 to indicate when the controller 28 receives power and a pump power indicator 36 to indicate when the controller 28 is providing power to the pump 10.

Figure 2:
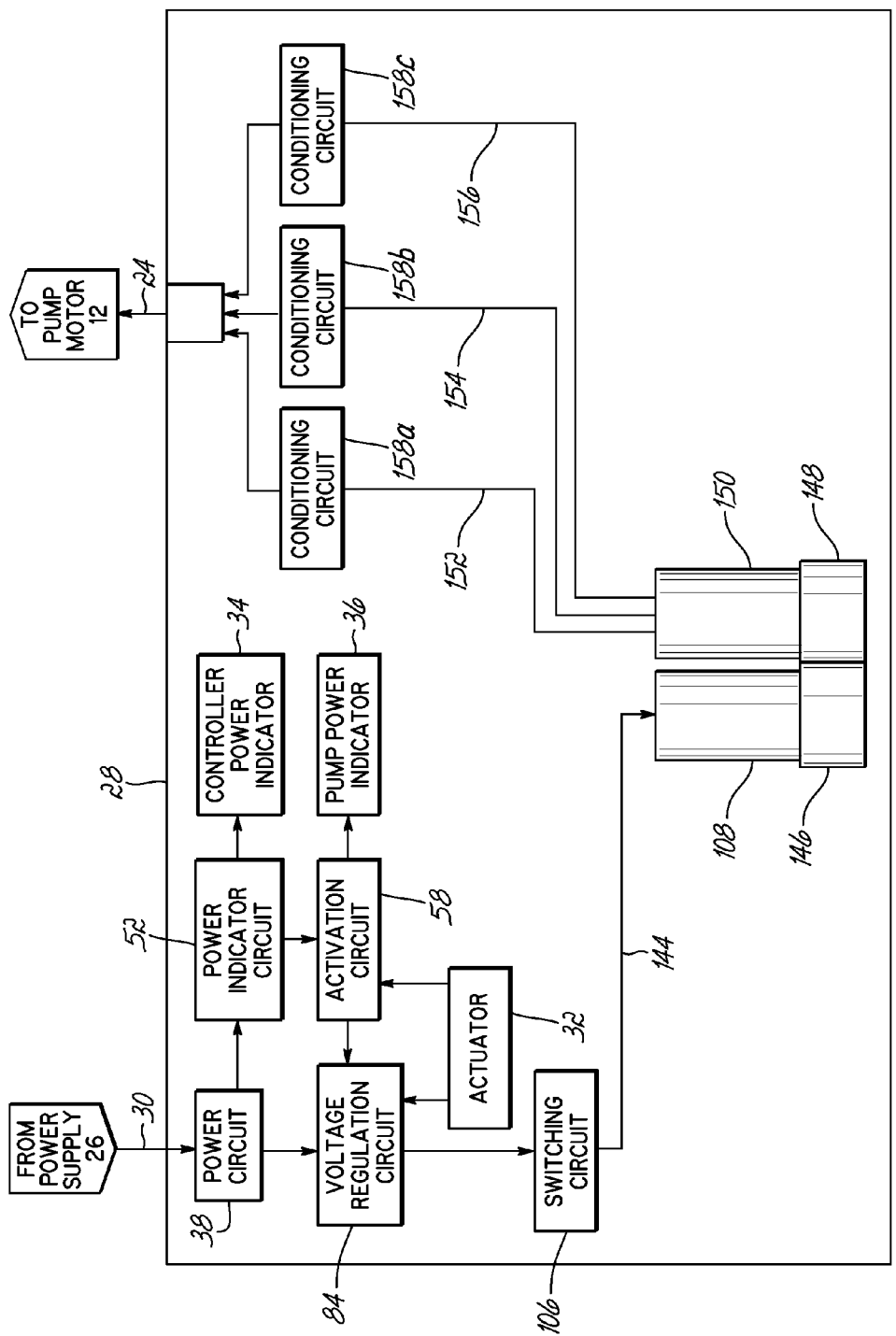
FIG. 2 is a diagrammatic illustration of one embodiment of the internal components of the test controller of FIG. 1.
Figure 3:
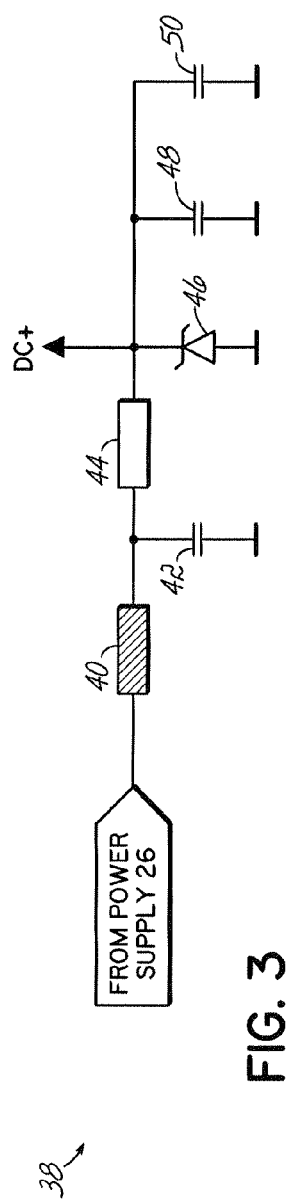
FIG. 3 is a diagrammatic illustration of one embodiment of a power circuit of the test controller of FIG. 1.

FIG. 2 is a diagrammatic illustration of one embodiment of internal components of the controller 28. The controller 28 includes a power circuit 38 that conditions power from the power supply 26 and converts at least a portion of the power to a direct current power signal to operate the circuitry of the controller 28. FIG. 3 is an illustration of one embodiment of the power circuit 38 that includes an inductor 40 that filters artifacts in power signals from the power supply 26 and that is coupled to a capacitor 42 and fuse 44. The capacitor 42 is coupled to ground and configured to allow alternating current signals from the power supply 26 to proceed to ground, while the fuse 44 is configured to prevent damage to the controller 28 in response to over-voltage or over-current power signals from the power supply 26. At the output of fuse 44, the power circuit 38 provides direct current power (illustrated as, and hereinafter, "DC+") for the controller 28 and is tied to a diode 46 as well as capacitors 48 and 50, capacitors 48 and 50 being configured in parallel and coupled to ground. Diode 46 is a voltage regulation diode, while capacitors 48 and 50 are configured to allow alternating current signals from the fuse 44 to proceed to ground. In specific embodiments, the inductor 40 has a resistance value of about 33 Ω at 100 MHz (about 0.008 Ω at zero Hz) and a current limit of about 4 A, the capacitor 42 has a value of about 100 nF, the capacitors 48 and 50 have a value of about 1 µf, the fuse 44 is a resettable fuse having a trip value of about 1.3 A, and the diode 44 has a value of about 22V and power limit of about 3 W. In further specific embodiments, the inductor 40 is a wide-band SMD ferrite bead, such as a WE-CBF 0805 4A 0R008 chip-inductor commercially available from Wurth Elektronik of Waldenburg, Germany.

Figure 4:
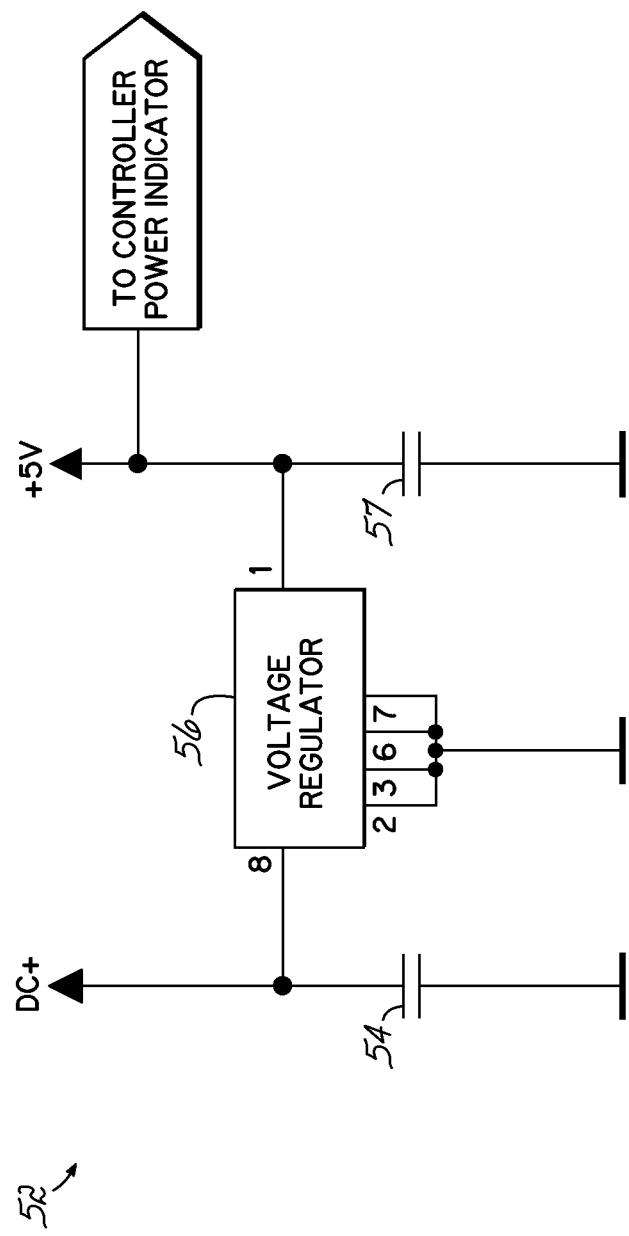
FIG. 4 is a diagrammatic illustration of one embodiment of a power indicator circuit of the test controller of FIG. 1.

Returning to FIG. 2, the power circuit 38 is configured to provide power to a power indicator circuit 52 that, in turn, is configured to activate the controller power indicator 34 when the controller 28 receives power from the power supply 26. FIG. 4 is an illustration of one embodiment of the power indicator circuit 52. As illustrated in FIG. 4, the power indicator circuit 52 receives the DC+ signal from the power circuit 38 and couples that signal to a capacitor 54 and a voltage regulator 56. The voltage regulator 56, in turn, regulates the DC+ signal and provide an output of 5V (illustrated as, and hereinafter, "+5V"). The output of the voltage regulator 56 is further coupled to another capacitor 57 and the controller power indicator 34. In specific embodiments, the voltage regulator 56 is an LM7B05 positive voltage regulator commercially available from Fairchild Semiconductor Corporation of South Portland, Me., and each of the capacitors 54 and 57 have a value of about 100 nF. As such, when power is provided to the controller 28 from the power supply 26, the power indicator circuit 52 is configured to activate the controller power indicator 34.

Figure 5:
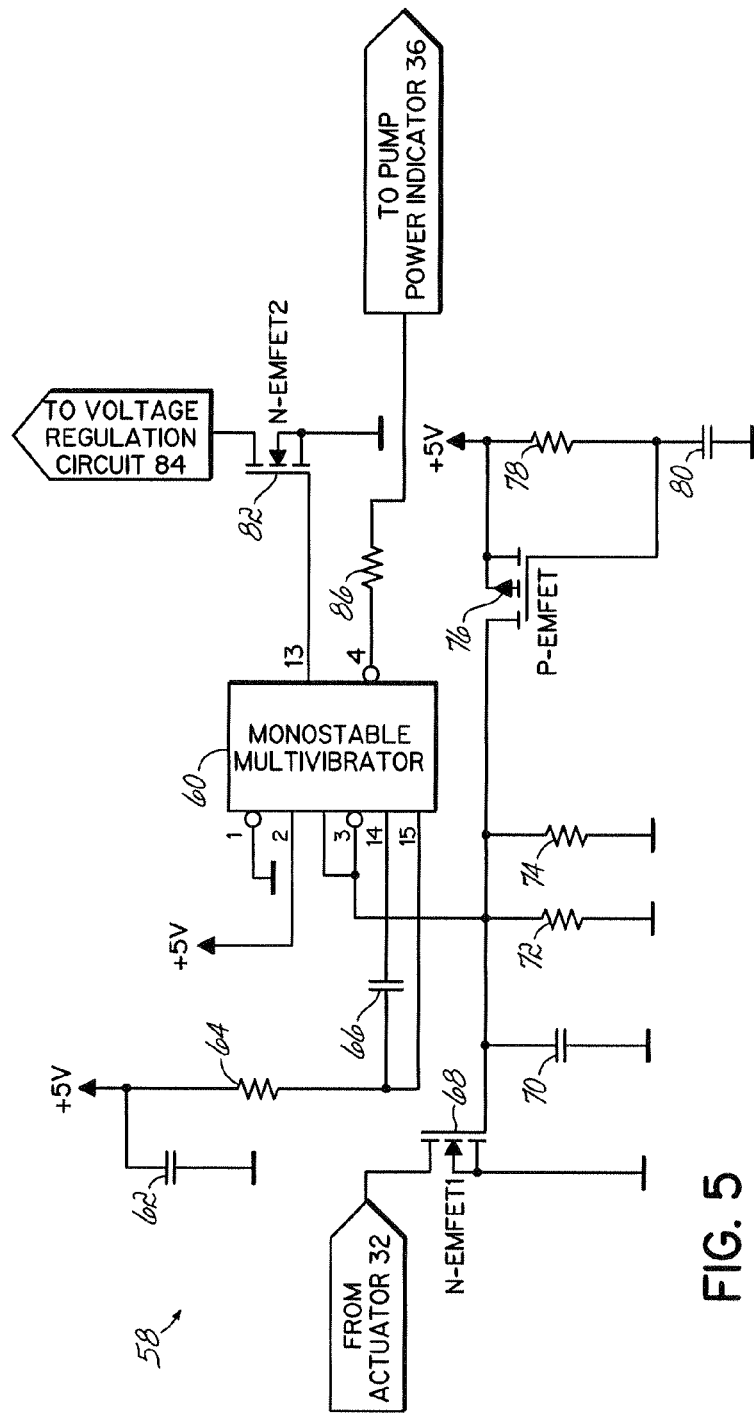
FIG. 5 is a diagrammatic illustration of one embodiment of an activation circuit of the test controller of FIG. 1.

Returning to FIG. 2, the power indicator circuit 52 is further coupled to an activation circuit 58 that activates the pump power indicator 36 in response to actuation of the actuator 32. FIG. 5 is an illustration of one embodiment of the activation circuit 58. Specifically, the activation circuit 58 is configured with a monostable multivibrator 60 that receives a +5V signal from the power indicator circuit 52 on a positive edge trigger input of the multivibrator 60 (e.g., pin 2) and an inverted ground signal on a negative edge trigger input of the multivibrator 60 (e.g., pin 1). Additionally, a +5V signal is coupled to a capacitor 62 and a resistor 64. One output from resistor 64 is coupled to a capacitor 66, while another output from the resistor 64 is coupled directly to an external resistor input of the multivibrator 60 (e.g., pin 15). The output of capacitor 66 is coupled to an external capacitor input of the multivibrator 60 (e.g., pin 14). The multivibrator 60 is further coupled to the actuator 32 through a first n-channel EMFET 68 (illustrated as, and hereinafter, "N-EMFET1" 68). In particular, the output of the actuator 32 is coupled to the drain of N-EMFET1 68, while the source is coupled to ground. The gate of N-EMFET1 68 is coupled to a capacitor 70, a resistor 72, and a resistor 74, all of which are in parallel. The gate of the N-EMFET1 68 is further coupled to an inverted reset low input of the multivibrator 60 (e.g., pin 3) and the drain of a p-channel EMFET 76 (illustrated as, and hereinafter, "P-EMFET" 76). In turn, the source of P-EMFET 76 is coupled to a +5V signal and the gate is coupled to a resistor 78 and capacitor 80. The resistor 78 is coupled between the source of P-EMFET 76 and the gate of P-EMFET 76, while the capacitor 80 is coupled to ground.

Thus, the multivibrator 60 is configured to detect actuation of the actuator 32 and provide a power signal to the pump power indicator 36, as well as selectively activate the pump motor 12 for a period of time from about four to about six seconds. As such, an active high output of the multivibrator 60 (e.g., pin 13) is coupled to the gate of a second n-channel EMFET 82 (illustrated as, and hereinafter, "N-EMFET2" 82). The source of N-EMFET2 82 is coupled to ground, while the drain of N-EMFET2 82 is configured to be coupled to a voltage regulation circuit 84. An inverted active low output of the multivibrator 60 (e.g., pin 4) is configured to provide power to the pump power indicator 36 when the pump motor 12 is supplied power through a resistor 86.

Figure 6:
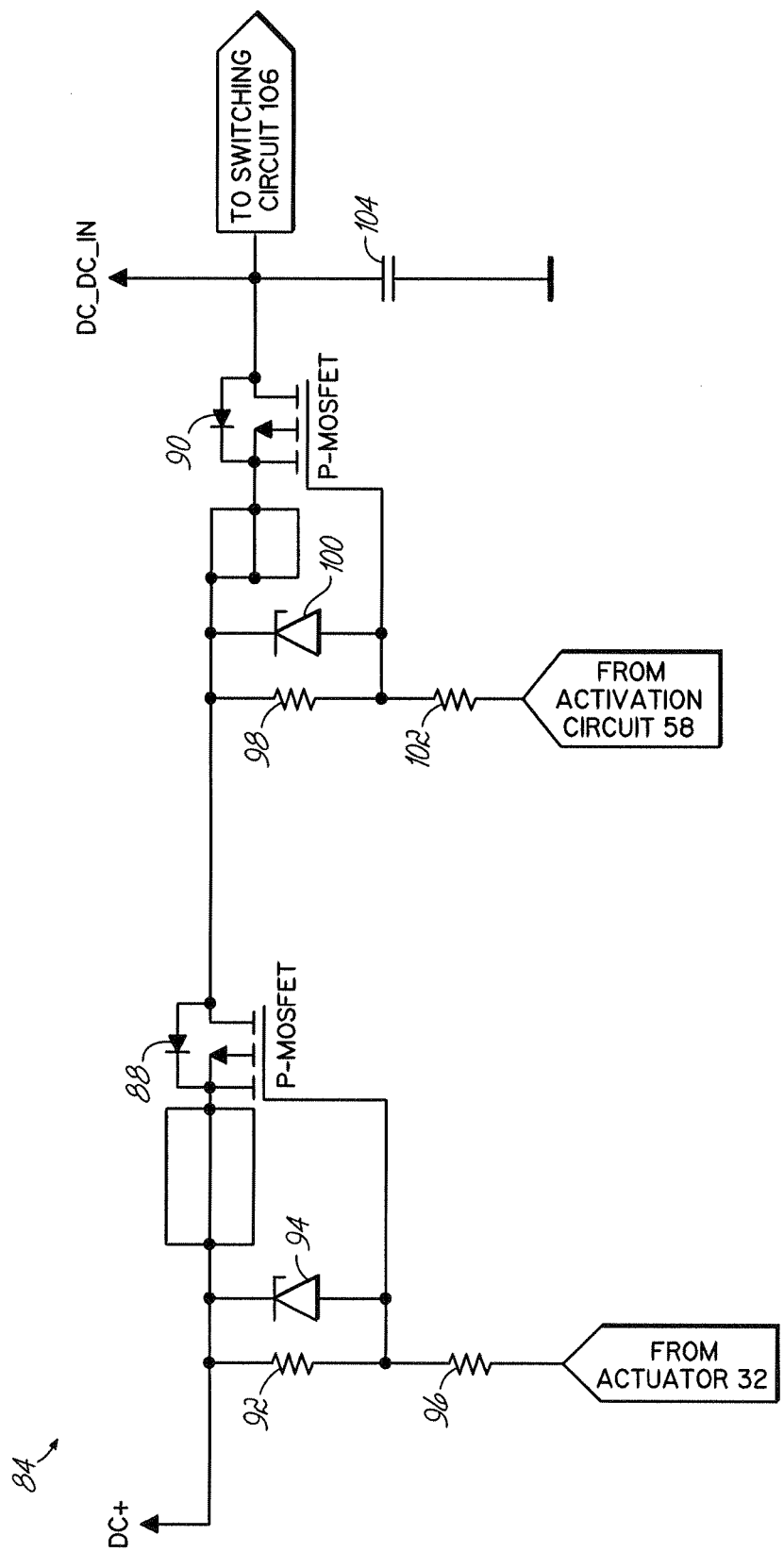
FIG. 6 is a diagrammatic illustration of one embodiment of a voltage regulation circuit of the test controller of FIG. 1.

Referring to FIG. 5, in specific embodiments, the monostable multivibrator 60 is a 74AHC123 dual retriggerable monostable multivibrator with reset as manufactured by NXP Semiconductor of the Netherlands. Also in specific embodiments N-EMFET1 68 and N-EMFET2 82 are each BSS123 n-channel EMFETs commercially available from Fairchild Semiconductor, while P-EMFET 76 is a BSS84 p-channel EMFET also commercially available from Fairchild Semiconductor. In further specific embodiments, the resistor 64 has a value of about 121 kΩ, the resistors 72 and 74 each have a value of about 21 kΩ, the resistor 78 has a value of about 10 kΩ, the resistor 86 has a value of about 1 kΩ, the capacitor 62 has a value of about 100 nF, the capacitors 66 and 70 each have a value of about 22 μF, and the capacitor 80 has a value of about 10 nF Referring back to FIG. 2, the power circuit 38 is coupled to the voltage regulation circuit 84, which is in turn coupled to the activation circuit 58 and the actuator 32. FIG. 6 is an illustration of one embodiment of the voltage regulation circuit 84. Specifically, the voltage regulation circuit 84 is configured with a pair of p-channel MOSFETS 88 and 90 (illustrated as, and hereinafter, "P-MOSFET1" 88 and "P-MOSFET2" 90). The DC+ from the power circuit 38 is coupled to a resistor 92 and a diode 94 in parallel. The DC+ is further coupled, through three parallel leads, to the source of P-MOSFET1 88. Additionally, the output from the actuator 32 is coupled, through a resistor 96, to the other end of the resistor 92, the input of diode 94, and the gate of P-MOSFET1 88. In turn, the drain of P-MOSFET1 88 is coupled to resistor 98 and diode 100 in parallel. The drain of P-MOSFET1 88 is further coupled, through three parallel leads, to the source of P-MOSFET2 90. Additionally, the signal from the activation circuit 58 is coupled, through resistor 102, to the other end of the resistor 98, the input of diode 100, and the gate of P-MOSFET2 90. The drain of P-MOSFET2 90 is then coupled to a capacitor 104, then output to a switching circuit 106. In specific embodiments, each resistor 92 and 98 has a value of about 22kΩ, each resistor 96 and 102 has a value of about 3kΩ, each diode 94 and 100 is a BZX284 series diode such as those commercially available from NXP, and each P-MOSFET 88 and 90 is an Si7415DN series p-channel 60-V MOSFET commercially available from Vishay Americas of Shelton, Conn.

Figure 7:
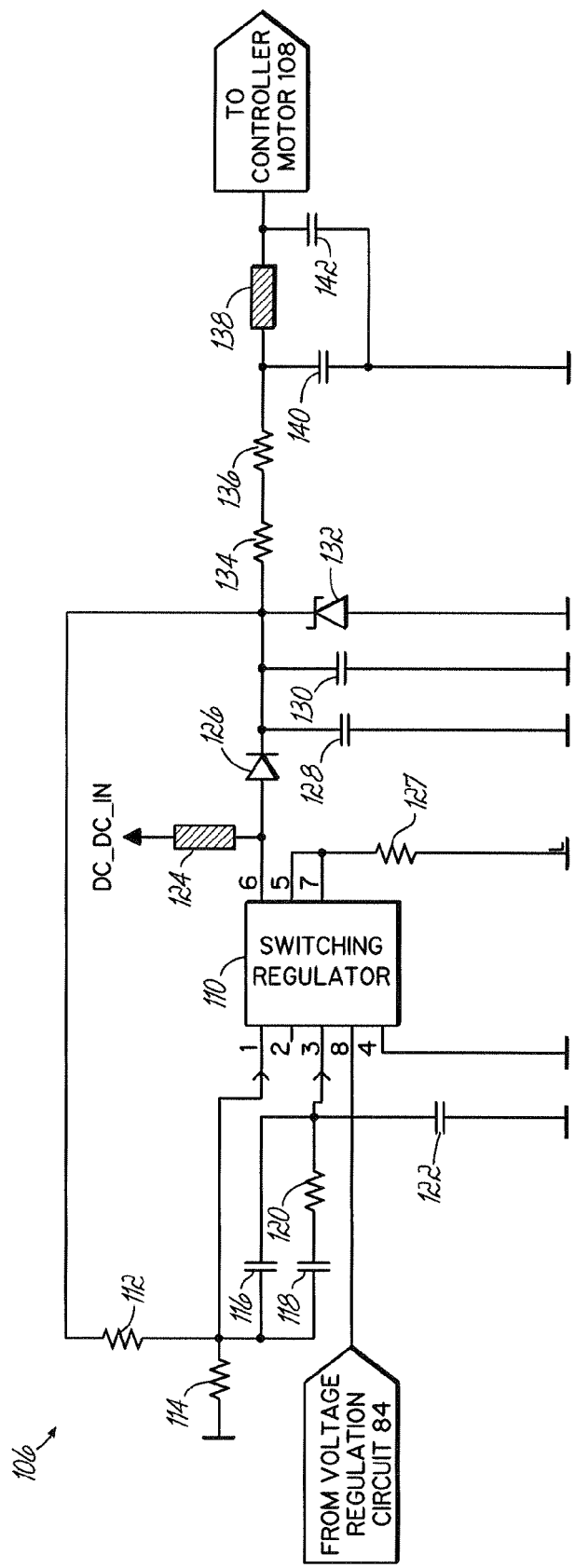
FIG. 7 is a diagrammatic illustration of one embodiment of a switching circuit of the test controller of FIG. 1.

Returning to FIG. 2, the switching circuit 106 is configured to transform a signal received from the voltage regulation circuit 84 into a signal appropriate for a controller motor 108. FIG. 7 is an illustration of one embodiment of the switching circuit 106 that includes a switching regulator 110 configured as a boost, or step-up regulator. Focusing on the inputs to the switching regulator, a voltage input of the switching regulator 110 (e.g., pin 8) is coupled to the voltage regulation circuit 84. Additionally, a corrective input of the switching regulator 110 (e.g., pin 1) is coupled to a resistor 112 configured as a feedback resistor from a collector output of the switching regulator 110 (e.g., pin 6) in parallel with a resistor 114. An oscillator input of the switching regulator 110 (e.g., pin 3) is connected to a capacitor 116 in parallel with a series combination of a capacitor 118 and a resistor 120. The capacitor 116 and series combination of capacitor 118 and resistor 120 are further in parallel with a capacitor 122 connected to ground. Furthermore, the opposite ends of the capacitor 116 and series combination of capacitor 118 and 120 are coupled to the parallel resistors 112 and 114. A ground input of the switching regulator 110 (e.g., pin 4) is connected to a ground.

Focusing on the outputs of the switching regulator 110, the collector output of the switching regulator 110 (e.g., pin 6) is coupled to an inductor 124 and a diode 126. The output of the inductor 124 is in turn coupled to the DC_DC_IN input. With regard to the emitter and current limit of the switching regulator 118 (e.g., pins 5 and 7, respectively), these are tied together as well as to a resister 127, which in turn is tied to ground.

The output of 126 is coupled to a capacitor 128 in parallel with a capacitor 130, both of which are tied to ground. The output of diode 126 is also coupled to the output of a diode 132 (whose input is tied to ground) as well as the resistor 112 that is coupled to the corrective input of the switching regulator 110 (e.g., pin 1). In addition, the output of diode 132 is coupled to two resistors 134 and 136 configured in series. The output of the resistors 134 and 136 is coupled to an inductor 138 and a capacitor tied 140 tied to ground. The output of the inductor 138 is in turn tied to another capacitor 142 as well as to the controller motor 108. In specific embodiments, the switching regulator 110 is an LM3578A series switching regulator commercially available from National Semiconductor of Santa Clara, Calif., the resistors 112 and 120 each have a value of about 200 kΩ, the resistor 114 has a value of about, the resistor 127 has a value of about 0 Ω, the resistors 134 and 136 each have a value of about 120 Ω, the capacitor 116 has a value of about 22 pF, the capacitor 118 has a value of about 33 nF, the capacitor 122 has a value of about 1 nF, the capacitor 128 has a value of about 10 μF, the capacitor 130 has a value of about 10 nF, the capacitor 140 has a value of about 100 nF, the capacitor 142 has a value of about 470 pF, the inductor 124 has a value of about 330 μH, the inductor 138 has a resistance value of about 33 Ω at 100 MHz (about 0.008 Ω at zero Hz) and a current limit of about 4 A, the diode 126 is a BZX284 series diode, and the diode 132 has a value of about 22V and power limit of about 3 W. In further specific embodiments, the inductor 138 is a WE-CBF 0805 4A 0R008 chip-inductor similarly to inductor 40 of FIG. 3.

Referring back to FIG. 2, an output 144 from the switching circuit 106 is coupled to the controller motor 108. The controller motor 108, in turn, is coupled to a first gearbox 146 which is mechanically coupled to a second gearbox 148 in turn coupled to a generator 150. The generator 150 is configured to provide three output lines 152, 154, and 156 to the pump motor 12 to provide respective "U," "V," and "W" phases for the pump motor 12. In specific embodiments, the controller motor 108 is an F 2140 series 40 mm graphite brushless DC motor commercially available from Maxon Precision Motors, Inc., of Fall River, Mass. In further specific embodiments, each of the gearboxes 146 and 148 are planetary gearheads series 16 A, 16 mm, also commercially available from Maxon, while the generator 150 is an EC 16 series 16 mm brushless EC motor, also commercially available from Maxon.

Figure 8:
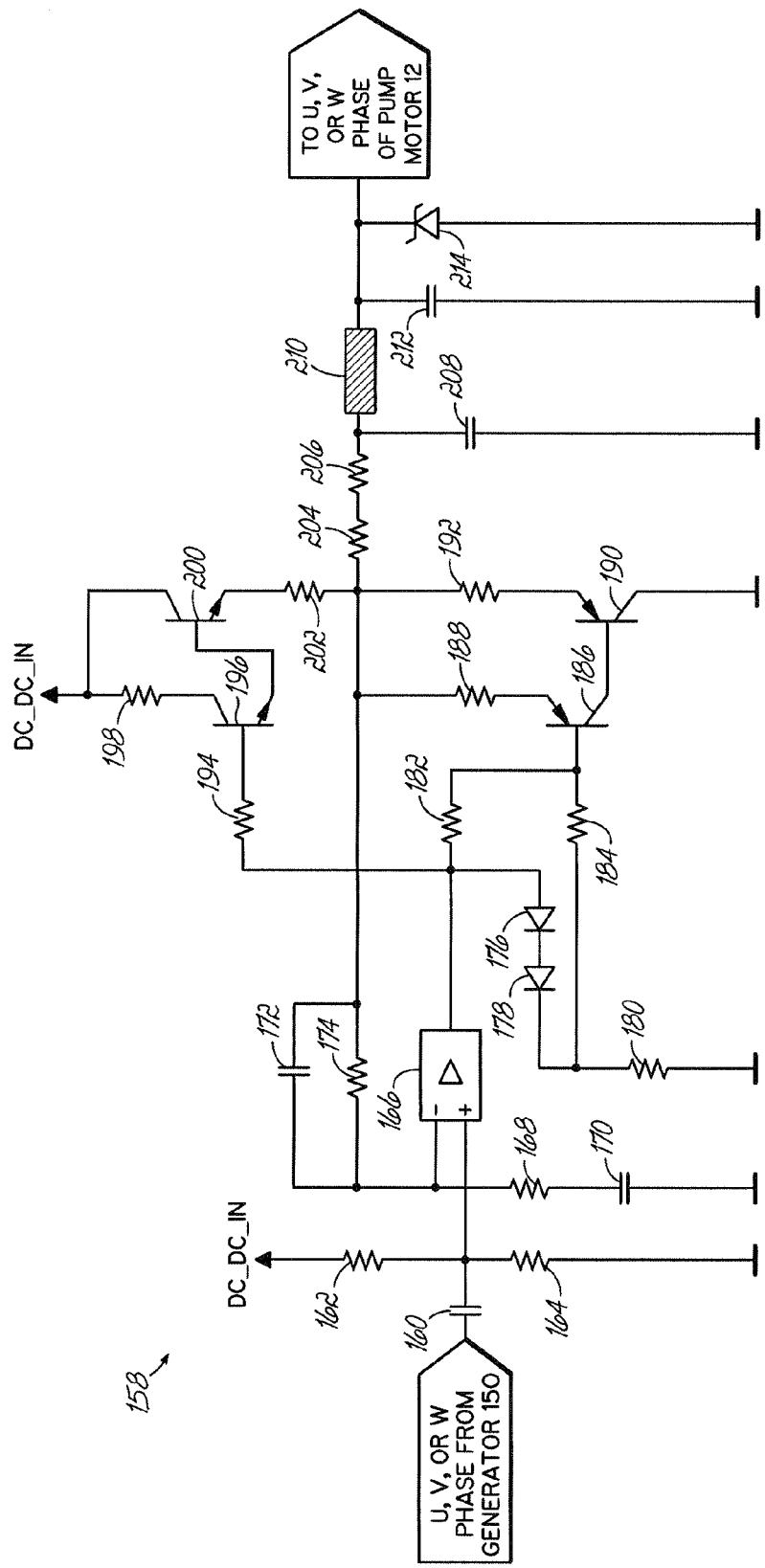
FIG. 8 is a diagrammatic illustration of one embodiment of a conditioning circuit of the test controller of FIG. 1.

In the controller 28, each of the phases for the pump motor 12 on the output lines 152, 154, and 156 is conditioned by a respective conditioning circuit 158a-c. FIG. 8 is an illustration of one embodiment of a conditioning circuit 158 that is used to condition a signal to the pump motor 12. Specifically, the input to the conditioning circuit 158 is a phase from the generator 150, which is coupled to a capacitor 160. The capacitor 160, in turn, is coupled to one resistor 162 coupled to the DC_DC_IN signal and one resistor 164 coupled to ground. The conditioning circuit 158 includes an operational amplifier 166, the positive input of which is coupled to the output of capacitor 160, the resistor 162 coupled to the DC_DC_IN signal, and the resistor 162 coupled to ground. The negative input of the amplifier 166 is coupled to the output of a series combination of a resistor 168 and a capacitor 170. The negative input of the amplifier 166 is further coupled to a capacitor 172 in parallel with a resistor 174. The output of the amplifier 166 is coupled to the input of a first diode 176, whose output is coupled to the input of a second diode 178. The output of the second diode 178 is, in turn, coupled to a resistor 180 tied to ground. Returning to the output of the amplifier 166, the output is also tied to a resistor 182 which is configured in parallel to a resistor 184 coupled to the output of the second diode 178. In turn, the resistors 182 and 184 are connected in parallel to the base of a first PNP transistor 186. The emitter of the first PNP transistor 186 is coupled to a resistor 188, which in turn is coupled to the parallel combination of the capacitor 172 and resistor 174 coupled to the negative input of the amplifier 166. The collector of the first PNP transistor 186, however, is tied to the base of a second PNP transistor 190. The emitter of the second PNP transistor 190 is coupled to a resistor 192, the resistor 192 being further coupled to the parallel combination of the capacitor 172 and resistor 174 coupled to the negative input of the amplifier 166.

The output of the amplifier 166 is also coupled to a resistor 194 that is coupled to the base of a first NPN transistor 196. The collector of the first NPN transistor 196 is coupled to a resistor 198. The resistor 198 is in turn coupled to the DC_DC_IN signal and the collector of a second NPN transistor 200. Returning to the first NPN transistor 196, the emitter of the first NPN transistor 196 is coupled to the base of the second NPN transistor 200. The emitter of the second NPN transistor 200 is coupled, through a resistor 202, to the parallel combination of capacitor 172 and resistor 174 coupled to the negative input of the amplifier 166.

As illustrated in FIG. 8, the parallel combination of capacitor 172 and resistor 174 coupled to the negative input of the amplifier 166 is further coupled to two resistors 204 and 206 in series. The output of the resistors 204 and 206, in turn, is coupled to a capacitor 208 tied to ground and an inductor 210. The inductor 210 is coupled, in parallel, to capacitor 212 tied to ground and the output of a diode 214 (the input being tied to ground). The inductor 210 is further tied to the U, V, or W phase of the pump motor 12.

In specific embodiments, the amplifier 166 is an AD824 series single supply, low power, FET-input op-amp commercially available from Analog Devices of Norwood, Mass. In further specific embodiments, the resistors 162, 164, and 174 each have a value of about 100 kΩ, the resistors 168, 188, and 198 each have a value of about 21 kΩ, the resistor 180 has a value of about 4 kΩ, the resistors 182, 184, and 194 each have a value of about 100 Ω, the resistors 192 and 202 each have a value of about 0 Ω, and the resistors 204 and 206 are each 4R7-5W series axial wirewound resistors. In specific embodiments, the capacitor 160 has a value of about 10 µF, the capacitor 170 has a value of about 4 µF, the capacitor 172 has a value of about 1 nF, the capacitor 208 has a value of about 47 µF, and the capacitor 212 has a value of about 100 nF. In specific embodiments, the ferrite bead 210 is a WE-CBF 0805 4A 0R008 chip-inductor similarly to inductor 40 of FIG. 3 and inductor 138 of FIG. 7, while the diodes 176 and 178 are each BAV99 series diodes commercially available from Fairchild Semiconductor and the diode 214 is a D402 series Zener diode.

When in use, an operator coupled the controller 28 to the pump 10 as well as to the power supply 26. When the controller 28 is supplied power, the controller power indicator 52 will be activated. When the user actuates the actuator 32, the controller transforms a power signal from the power supply 26 into a plurality of signals for the pump motor 12. Specifically, the controller 28 is configured to operate the pump motor 12 from a speed of about 780 RPM to about 1,180 RPM, whereas during normal operation the pump motor 12 is configured to operate at a speed from about 20,000 RPM to a speed of about 28,000 RPM. Moreover, the controller 28 is configured to provide enough power to the pump motor 12 such that the pump motor 12 can utilize back-EMF control methodologies without causing the pump motor 12 to stop or suffer from overspeed. Thus, the user can visually verify the operation of the pump 10 without utilizing a sterile bath.

The controller 28 is configured to transform power from the power supply 26 for the pump 10 for a period of time from about four to about six seconds. Specifically, the controller 28 is configured to provide power to the pump 10 when the actuator 32 is continuously actuated, but for no more than that period of time. Alternatively, the controller 28 can be configured to provide power to the pump 10 for that period of time in response to a momentary actuation of the actuator 32. When the controller 28 provides power to the pump 10, the pump power indicator 34 is activated. After the user has completed their inspection, the user can detach the controller 28 from the pump 10 and the power supply 26.

While embodiments of the present invention has been illustrated by a description of the various embodiments and the examples, and while these embodiments have been described in considerable detail, it is not the intention of the applicants to restrict or in any way limit the scope of the appended claims to such detail. Additional advantages and modifications will readily appear to those skilled in the art. Thus, embodiments of the present invention in broader aspects are therefore not limited to the specific details, representative apparatus and method, and illustrative example shown and described. Accordingly, departures may be made from such details without departing from the spirit or scope of applicants' general inventive concept.

What is claimed is:

1. A test controller for operating a rotary pump motor of a pump configured for implantation into a patient and that operates in the implanted state without the test controller, the rotary pump motor having a normal operating speed, comprising:
   a test speed circuit electrically coupled to, but detachable from, the pump and being configured to apply at least one signal to the pump motor to cause the pump motor to rotate at a predetermined test speed that is lower than the normal operating speed of the pump motor; and
   an actuator configured to selectively activate the test speed circuit to operate the pump motor to rotate at the predetermined test speed in response to selective activation of the actuator by a user.

2. The test controller of claim 1, wherein the normal operating speed is from about 20,000 rotations-per-minute to about 28,000 rotations-per-minute, and the predetermined test speed is from about 780 rotations-per-minute to about 1180 rotations-per-minute.

3. The test controller of claim 1, further comprising:
a timing circuit electrically coupled to the test speed circuit and the actuator, the timing circuit operating with the test speed circuit and the actuator to discontinue the at least one signal to the pump motor after a predetermined period of time in response to continuous activation of the actuator.

4. The test controller of claim 3, wherein the predetermined period of time is from about four to about six seconds.

5. The test controller of claim 1, wherein the test speed circuit is configured to produce the at least one signal during selective activation of the actuator.

6. The test controller of claim 1, wherein the test speed circuit is electrically coupled to, but detachable from, a power supply for the pump to transform a power signal from the power supply into the at least one signal.

7. The test controller of claim 1, wherein the pump includes an impeller.

8. A test controller for operating a rotary pump motor of a pump configured for implantation into a patient and that operates in the implanted state without the test controller, the rotary pump motor having a predetermined operating speed, comprising:
a test speed circuit electrically coupled to, but detachable from, the pump and being configured to apply at least one signal to the pump motor to cause the pump motor to rotate for a predetermined test time; and
an actuator configured to selectively activate the test speed circuit to operate the pump motor to rotate for the predetermined test time in response to selective activation of the actuator by a user.

9. The test controller of claim 8, wherein the predetermined test time is from about four to about six seconds.

10. The test controller of claim 8, wherein the speed circuit is further configured to apply the at least one signal to the pump motor to operate the pump motor to rotate at a predetermined test speed.

11. The test controller of claim 10, wherein the predetermined test speed is from about 780 rotations-per-minute to about 1180 rotations-per-minute.

12. The test controller of claim 8, further comprising:
a timing circuit electrically coupled to the test speed circuit and the actuator, the timing circuit operating with the test speed circuit and the actuator to discontinue the at least one signal to the pump motor after a predetermined period of time in response to continuous activation of the actuator.

13. The test controller of claim 8, wherein the test speed circuit is configured to apply the at least one signal during selective activation of the actuator.

14. The test controller of claim 8, wherein the pump includes an impeller.

15. A method for testing the operation of a rotary pump motor of a pump configured for implantation into a patient with a test controller, the rotary pump motor having a predetermined operating speed and the test controller including a test speed circuit and an actuator, the method comprising:
electrically coupling the test controller to the pump;
in response to selective activation of the actuator, selectively activating the test speed circuit to apply at least one signal to the pump motor to cause the pump motor to rotate at a predetermined test speed that is lower than a predetermined operating speed of the pump motor; and
detaching the test controller from the pump.

16. The method of claim 15, wherein the predetermined operating speed is from about 20,000 rotations-per-minute to about 28,000 rotations-per-minute, and the predetermined test speed is from about 780 rotations-per-minute to about 1180 rotations-per-minute.

17. The method of claim 15, wherein the at least one signal is applied for a predetermined time.

18. The method of claim 17, wherein the predetermined time is from about four seconds to about six seconds.

19. The method of claim 15, further comprising:
electrically coupling the test controller to a power supply for the pump; and
transforming a power signal from the power supply into the at least one signal.

20. The method of claim 15, wherein the pump includes an impeller.

21. A method for testing the operation of a rotary pump motor of a pump configured for implantation into a patient with a test controller, the rotary pump motor having a predetermined operating speed and the test controller including a test speed circuit and an actuator, the method comprising:
electrically coupling the test controller to the pump; and
in response to selective activation of the actuator, selectively activating the test speed circuit to apply at least one signal to the pump motor to cause the pump motor to rotate for a predetermined test time; and
detaching the test controller from the pump.

22. The method of claim 21, wherein the predetermined test time is from about four seconds to about six seconds.

23. The method of claim 21, wherein the at least one signal causes the pump motor to rotate at a predetermined test speed that is lower than a predetermined operating speed of the pump motor.

24. The method of claim 23, wherein the predetermined operating speed is from about 20,000 rotations-per-minute to about 28,000 rotations-per-minute, and the predetermined test speed is from about 780 rotations-per-minute to about 1180 rotations-per-minute.

25. The method of claim 21, further comprising:
electrically coupling the test controller to a power supply for the pump; and
transforming a power signal from the power supply into the at least one signal.

26. The method of claim 21, wherein the pump includes an impeller.

27. The test controller of claim 12, wherein the predetermined time is from about four seconds to about six seconds.

28. The method of claim 15, wherein the selective activation of the actuator is by a user.

29. The method of claim 28, further comprising:
discontinuing the at least one signal to the pump motor after a predetermined period of time in response to activation of the actuator, wherein detaching the test controller from the pump occurs after discontinuing the at least one signal to the pump motor.

30. The method of claim 21, wherein the selective activation of the actuator is by a user.

* * * * *